United States Patent
Eisenkolb et al.

(10) Patent No.: US 9,164,270 B2
(45) Date of Patent: Oct. 20, 2015

(54) ENDOSCOPE WITH PIVOTABLE VIEWING DIRECTION

(71) Applicant: Karl Storz GmbH & Co. KG, Tuttlingen (DE)

(72) Inventors: Peter Eisenkolb, Tuttlingen (DE); Stefan Heseler, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 87 days.

(21) Appl. No.: 13/891,526

(22) Filed: May 10, 2013

(65) Prior Publication Data
US 2013/0322092 A1 Dec. 5, 2013

Related U.S. Application Data

(63) Continuation of application No. PCT/EP2011/005683, filed on Nov. 11, 2011.

(30) Foreign Application Priority Data

Nov. 11, 2010 (DE) .................. 10 2010 050 933

(51) Int. Cl.
*A61B 1/06* (2006.01)
*G02B 23/24* (2006.01)
*A61B 1/00* (2006.01)
*A61B 1/07* (2006.01)

(52) U.S. Cl.
CPC ........ *G02B 23/2461* (2013.01); *A61B 1/00096* (2013.01); *A61B 1/00181* (2013.01); *A61B 1/07* (2013.01); *G02B 23/2423* (2013.01); *G02B 23/2469* (2013.01)

(58) Field of Classification Search
CPC ........... G02B 7/00; G02B 17/00; G02B 26/00
USPC ................... 362/572, 576, 577, 560; 600/104
See application file for complete search history.

(56) References Cited

U.S. PATENT DOCUMENTS

| | | | | |
|---|---|---|---|---|
| 3,880,148 A * | 4/1975 | Kanehira et al. | ........... | 600/173 |
| 4,140,364 A * | 2/1979 | Yamashita et al. | ........... | 359/367 |
| 4,195,904 A * | 4/1980 | Yamashita | ........... | 359/367 |
| 4,730,909 A * | 3/1988 | Takahashi | ........... | 359/735 |
| 6,560,013 B1 * | 5/2003 | Ramsbottom | ........... | 359/431 |
| 7,758,224 B2 * | 7/2010 | Hama et al. | ........... | 362/555 |
| 7,980,745 B2 * | 7/2011 | Shanbaky | ........... | 362/581 |
| 8,358,067 B2 * | 1/2013 | Kamee et al. | ........... | 313/583 |
| 8,488,930 B2 * | 7/2013 | Papac et al. | ........... | 385/116 |
| 8,556,471 B2 * | 10/2013 | Pahlke et al. | ........... | 362/328 |
| 8,801,204 B2 * | 8/2014 | Kamee et al. | ........... | 362/84 |

* cited by examiner

*Primary Examiner* — Ali Alavi
(74) *Attorney, Agent, or Firm* — Whitmyer IP Group LLC

(57) ABSTRACT

An endoscope having a viewing direction which can be pivoted relative to the endoscope includes an illumination beam path for transmitting illumination light and a plurality of reflective surfaces for reflecting illumination light, the reflective surfaces being arranged at least partially next to one another in the illumination beam path relative to the intended light propagation direction of illumination light in the illumination beam path.

14 Claims, 2 Drawing Sheets

ENDOSCOPE WITH PIVOTABLE VIEWING DIRECTION

FIELD OF THE INVENTION

The present invention relates to an endoscope having a pivotable viewing direction.

BACKGROUND OF THE INVENTION

Besides endoscopes for medical and non-medical technical applications, the viewing direction of which is parallel to the longitudinal axis of the shaft of the endoscope, endoscopes having different fixed viewing directions were already developed early on. Here and in what follows, the viewing direction of an endoscope always means the direction from the distal end of the endoscope in which an object, which appears in the middle of the image acquired by means of the endoscope, lies. In many applications, however, a fixed viewing direction is disadvantageous. In the least favorable case, for example, the endoscope must be changed several times during a medical intervention. In such cases, the use of an endoscope having an in-situ adjustable or variable viewing direction is advantageous.

The observation of an object in a cavity by means of an endoscope generally requires illumination of the object. To this end, for example, an endoscope comprises light waveguides, in particular glass fibers, by means of which illumination light is transmitted from the proximal end of the endoscope along the shaft to the distal end of the endoscope. Light exit surfaces of the light waveguides at the distal end of the endoscope are arranged and formed in such a way that the entire field of view, or viewing field, is illuminated sufficiently.

In order to illuminate the entire field of view for all possible viewing directions, a plurality of light exit surfaces, through which illumination light emerges in different directions, are for example provided. At these light exit surfaces, light waveguides sometimes have curvatures with small radii immediately proximally with respect to the light exit surface. At least when changing to ever smaller shaft diameters, however, the radii of curvature are simply so small that fracture of the light waveguides is no longer the exception but the rule. When the radius of curvature is too small, furthermore, the light guiding properties of a light waveguide are lost.

DE 600 15 375 T2 describes an arrangement of a plurality of prisms. One of the prisms can be rotated about an axis in order to shine illumination light in an adjustable viewing direction. This arrangement, however, can only be miniaturized further with great outlay. For endoscopes with ever thinner shafts, alternative concepts that can be miniaturized further are necessary.

SUMMARY OF THE INVENTION

It is an object of the present invention to provide an improved endoscope having a pivotable viewing direction.

This object is achieved by the subject-matter of the independent claims.

Refinements are specified in the dependent claims.

The present invention is based on the idea, in an endoscope having an adjustable viewing direction, of providing a plurality of reflective surfaces, arranged at least partially next to one another in the illumination beam path, in order to illuminate all possible fields of view of the endoscope. By virtue of the plurality of reflective surfaces, the illumination light can be fanned out in order to illuminate a large angle range, at least in one direction.

An endoscope having a viewing direction which can be pivoted relative to the endoscope comprises an illumination beam path for transmitting illumination light and a plurality of reflective surfaces for reflecting illumination light, the reflective surfaces being arranged at least partially next to one another in the illumination beam path relative to the intended light propagation direction of illumination light in the illumination beam path.

The viewing direction of the endoscope can, in particular, be pivoted about a pivot axis which is perpendicular to the longitudinal axis of the endoscope, or at least not parallel to the longitudinal axis of the endoscope. The endoscope may have one or more light-emitting diodes, or one or more light sources, at the distal end or at the proximal end. In this case, the illumination beam path extends from the light source or sources to one or more illumination windows at the distal end of the endoscope. Alternatively, the illumination beam path extends from a coupler at the proximal end of the endoscope to one or more illumination windows at the distal end of the endoscope, the coupler being formed in order to couple the endoscope to a light source by means of a light guide cable. For transmission of illumination light from the proximal end to the distal end of the endoscope, the latter comprises for example a light waveguide, a bundle of light waveguides or a different light guide.

The cross section of the illumination beam path is, in particular, simply connected immediately optically upstream of the reflective surfaces. The endoscope may comprise a plurality of illumination beam paths, a plurality of reflective surfaces being arranged inside each individual illumination beam path, at least partially next to one another in relation to the intended light propagation direction. In particular, the endoscope comprises two or more illumination beam paths on opposite sides of an observation beam path, light exit surfaces of a first illumination beam path and light exit surfaces of a second illumination beam path being arranged on opposite sides of a light entry surface of the observation beam path at the distal end of the endoscope.

The intended light propagation direction of illumination light is from the light source or from the proximal end of the endoscope to the light exit surface or surfaces at the distal end of the endoscope. The reflective surfaces extend, in particular, at least partially essentially parallel to the intended light propagation direction. Since in reality illumination light comes from an extended light source, not a point light source, it never propagates entirely parallel in an illumination beam path having a finite cross section. For this reason, for example, the average light propagation direction within the cross section of the illumination beam path is regarded as the light propagation direction.

In particular, the reflective surfaces divide the cross section of the illumination beam path into a plurality of partial cross sections. Owing to a fanning effect of the reflective surfaces on the illumination light, the light propagation direction (again in the sense of an average light propagation direction within the relevant partial cross section) may differ between each pair of neighboring reflective surfaces.

The criterion of the arrangement of a first reflective surface and a second reflective surface at least partially next to one another relates, in particular, to the light propagation directions immediately optically upstream and immediately optically downstream of the edges, arranged optically upstream, of the reflective surfaces. In this case, the light propagation direction is only insubstantially altered immediately optically downstream of the optically upstream edge of a reflective surface, because only a small part of the illumination light is already reflected at the reflective surface.

A first reflective surface and a second reflective surface are arranged at least partially next to one another in the illumination beam path, in relation to the intended light propagation direction of the illumination light in the illumination beam path, when they are arranged next to one another relative to the light propagation direction immediately optically upstream and relative to the light propagation direction immediately optically downstream of the optically upstream edge of the first reflective surface, and in relation to the light propagation direction immediately optically upstream and in relation to the light propagation direction immediately optically downstream of the optically upstream edge of the second reflective surface. Relative to a direction, two reflective surfaces lie next to one another when a plane perpendicular to the direction intersects both reflective surfaces. In particular, planes which are perpendicular to the light propagation directions and which intersect the reflective surfaces on their optically upstream edges or close to their optically upstream edges are considered.

Already from an intuitive understanding, the reflective surfaces of the prisms described in DE 600 15 375 T2 mentioned above are correspondingly not arranged at least partially next to one another in the sense of the present invention. Illumination light cannot simultaneously strike the two reflective surfaces of the prisms. Rather, illumination light is first deviated through 90 degrees by the reflective surface of a first prism and then once more deviated through 90 degrees by the reflective surface of a second prism. The arrangement is formed so that illumination light which strikes the second reflective surface has previously been deviated through 90 degrees by the first reflective surface. The reflective surfaces are thus arranged not next to one another but successively in relation to the light propagation direction.

The reflective surfaces of the prisms according to DE 600 15 375 T2 are also not arranged next to one another in relation to the aforementioned criteria for an arrangement of reflective surfaces at least partially next to one another. Although there are planes which are intersected by the reflective surfaces of both prisms, there is for example no plane, perpendicular to the light propagation direction between the two reflective surfaces, which intersects both reflective surfaces.

The plurality of reflective surfaces permits widening, or fanning, of the illumination light at least within one direction, and therefore illumination of all possible fields of view of an endoscope having a pivotable viewing direction. The arrangement of a plurality of reflective surfaces can be miniaturizable with little or comparative outlay. Since the reflective surfaces can be arranged rigidly, or immobile, it is also possible to achieve great mechanical robustness and stability in relation to sterilization processes in an autoclave.

In an endoscope as described here, the reflective surfaces may be arranged in the shape of a fan.

The reflective surfaces are, in particular, arranged in the shape of a fan when their spacings increase in one direction. In particular, their spacings increase in the light propagation direction.

If the reflective surfaces are planar, they are arranged in the shape of a fan in particular when all planes in which the reflective surfaces lie intersect on a single straight line or on a plurality of parallel straight lines, the maximum distance between two parallel lines of intersection being not greater than the linear dimensions of the reflective surfaces in a direction perpendicular to the lines of intersection, or not greater than one half, one third or one fifth of this dimension.

The fan-shaped arrangement of the reflective surfaces permits widening, or fanning, of the illumination light in one direction. The distribution of the illumination light can be adjusted by means of the number, size and configuration of the reflective surfaces and their angular spacings.

In an endoscope as described here, the surface normals of planar reflective surfaces of the plurality of reflective surfaces may lie in a plane perpendicular to a pivot axis of the viewing direction.

In particular, all reflective surfaces of the plurality of reflective surfaces are planar and the surface normals of all reflective surfaces lie in a plane perpendicular to the pivot axis of the viewing direction. Alternatively, only a subset of the reflective surfaces are planar, the surface normals of all planar reflective surfaces, or at least the surface normals of a plurality of planar reflective surfaces, lying in a plane perpendicular to a pivot axis of the viewing direction.

In an endoscope as described here, local surface normals of reflective surfaces in the central regions of the reflective surfaces may lie in a plane perpendicular to a pivot axis of the viewing direction.

The formation and arrangement of planar or curved reflective surfaces in such a way that the surface normals, or in the case of curved reflective surfaces the local surface normals in central regions of the reflective surfaces, lie in a plane perpendicular to the pivot axis of the viewing direction can permit precise fanning of the illumination light in the pivot direction. The distribution of the illumination light can be adjusted by means of the number, size, configuration and, in particular, curvature of the reflective surfaces.

In an endoscope as described here, a reflective surface of the plurality of reflective surfaces may have a reflectance of at most 0.75.

In particular, the reflective surface has, or a plurality of or all reflective surfaces of the plurality of reflective surfaces have, a reflectance of at most 0.75, at most 0.50 or at most 0.25. A reflectance of the reflective surfaces which is significantly less than 1 can permit more refined fanning of the illumination light and a particularly high uniformity of the intensity of the illumination light. This may, in particular, be contributed to in that illumination light is not only reflected forward and back between two directly neighboring reflective surfaces, but is also partially reflected successively at a plurality of different reflective surfaces.

An endoscope as described here may comprise a light distribution device which comprises a plurality of transparent bodies, the reflective surfaces being present at interfaces respectively between two adjacent transparent bodies.

The transparent bodies may be prisms made of a transparent material.

A prism is intended in particular to mean a prism in the strict geometrical sense, i.e. a body having two opposite parallel and identical bounding surfaces, the other bounding surfaces of which are parallelograms. In optics, the term prism is often used in the wider sense, in order to denote transparent bodies whose surfaces have at least two non-parallel planar sections through which light enters in a first direction and emerges in a second direction. As a further generalization, the light distribution device of the endoscope as described here may comprise a plurality of non-prismatic transparent bodies.

Forming the reflective surfaces at interfaces between transparent bodies cemented, for example, to one another can be particularly robust and at the same time substantially miniaturizable. The reflective surfaces are protected by the transparent bodies, and the light distribution device forms a compact and mechanically robust component which is easy to mount.

In an endoscope as described here having a light distribution device, sections of a light exit surface of the light distribution device, which adjoin individual transparent bodies of the light distribution device, may be planar.

Alternatively, in an endoscope as described here having a light distribution device, sections of a light exit surface of the light distribution device, which adjoin individual transparent bodies of the light distribution device, may be curved.

In a simple case, each transparent body has a planar or, for example, cylindrically or elliptically or spherically or torically curved surface, which adjoins two different reflective surfaces of the plurality of reflective surfaces at opposite edges, and which forms a section of the light exit surface of the light distribution device. The distribution of the illumination light, or of its intensity, can be improved further by the planar or curved configuration of these sections of the light exit surface.

In an endoscope as described here having a light distribution device, sections of a light entry surface of the light distribution device, which adjoin individual transparent bodies of the light distribution device, may be planar.

Alternatively, sections of a light entry surface of the light distribution device, which adjoin individual transparent bodies of the light distribution device, are curved.

In a simple case, a transparent body has a planar, cylindrically, torically, elliptically, spherically or otherwise curved surface section, which adjoins two reflective surfaces at opposite edges, and which forms a section of the light entry surface of the light distribution device. The distribution of the illumination light can be improved by the configuration of the light entry surface. In particular, a convexly curved light entry surface of the light distribution device can have a collimating effect. Alternatively, a divergence or convergence of the illumination light can be adjusted by a correspondingly curved light entry surface of the light distribution device, or one which is formed in a planar fashion locally or overall. The light entry surface may furthermore be welded, adhesively bonded or otherwise joined to a light-emitting diode or another light source, or to a light exit surface of a light guide. This allows permanent and permanently precise alignment of the light source, or the light exit surface of the light guide, relative to the light distribution device.

In an endoscope as described here, the reflective surfaces may be at least either pivotable about an axis or displaceable along a path.

With corresponding configuration of the reflective surfaces, even minor pivoting or displacement can permit modification of the solid angle range illuminated by means of the reflective surfaces. In particular when the endoscope has a light distribution device as described above, the latter can simultaneously be formed robustly and pivotably or displaceably in a simple and precise way.

In an endoscope in which the reflective surfaces are at least either pivotable about an axis or displaceable along a path, the illumination of the reflective surfaces is in particular dependent on the position of the reflective surfaces adjusted by pivoting or displacing the reflective surfaces.

In particular, it is possible to adjust which reflective surface illumination light strikes or at which angle illumination light strikes a reflective surface, or at which angles illumination light strikes a plurality of reflective surfaces. In this way, the solid angle range illuminated by illumination light can be adjusted.

BRIEF DESCRIPTION OF THE DRAWINGS

Embodiments will be explained in more detail below with the aid of the appended figures, in which.

DETAILED DESCRIPTION OF THE INVENTION

Figure 1:
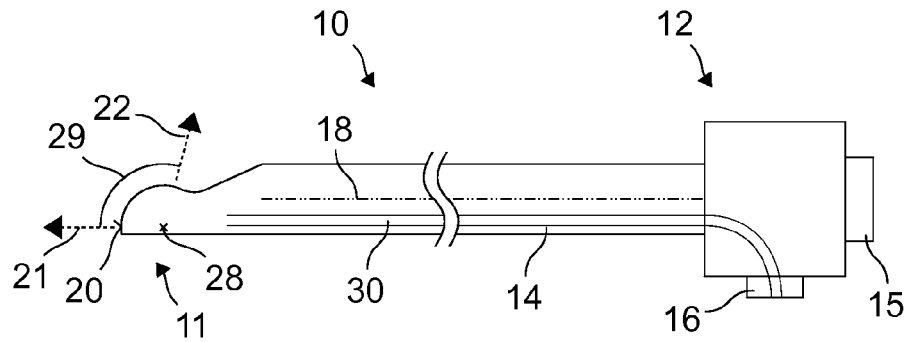
FIG. 1 shows a schematic representation of an endoscope having an adjustable viewing direction.

FIG. 1 shows a schematic representation of an endoscope 10 having a distal end 11, a proximal end 12, and a rigid shaft 14 which extends from the distal end 11 to the proximal end 12. Alternatively, the shaft 14 is flexible or partially flexible. The cross section of the shaft 14, or at least the outer contour of the cross section of the shaft 14, is constant or essentially constant between the distal end 11 and the proximal end 12. In particular, the contour of the cross section of the shaft 14 is circular or elliptical. In this case, the longitudinal axis 18 of the endoscope 10, as represented in FIG. 1, is the symmetry axis of the lateral surface of the shaft 14 between the distal end 12 and the proximal end 11. In the case of a cylindrical lateral surface of the shaft 14, the longitudinal axis 18 is also the set of midpoints or area centroids of the cross sections of the shaft 14 between the distal end 12 and the proximal end 11. In the case of a circular-cylindrical lateral surface of the shaft 14, the longitudinal axis 18 is also the symmetry axis of the lateral surface.

At the distal end 12, the configuration of the shaft 14 departs from cylindrical symmetry, as represented by way of example in FIG. 1. In particular, the shaft 14 has, at the distal end 12, an opening which is closed by a transparent window component having a curved surface 20. In particular, the window component 20 closes the opening in a hermetically sealed fashion. The surface 20 of the window component has, for example, the configuration of a section of a circular-cylindrical lateral surface, the symmetry axis of the circular cylinder being perpendicular to the longitudinal axis 18 of the endoscope 10 and to the plane of the drawing of FIG. 1. Alternatively, the surface 20 of the transparent window component has the configuration of a section of a spherical surface or of a rotationally symmetrical or rotationally non-symmetrical ellipsoid.

At the distal end 12 of the endoscope 10, optical devices (not represented in FIG. 1) are arranged in the shaft 14. These optical devices permit variation of the viewing direction of the endoscope between a first extreme viewing direction 21 and a second extreme viewing direction 22. The viewing direction can be pivoted between the two extreme viewing directions 21, 22 about a pivot axis 28, which is perpendicular to the plane of the drawing of FIG. 1. The viewing direction is respectively the direction relative to the distal end 12 of the endoscope 10 in which an object, which appears in the middle of an image acquired by means of the endoscope 10, lies.

In the example represented in FIG. 1, the first extreme viewing direction 21 is parallel or essentially parallel to the longitudinal axis 18 of the endoscope 10. Between the extreme viewing directions 21, 22, there is an angle range 29, which covers approximately 120 degrees in the example represented. The viewing direction of the endoscope 10 is adjustable, in particular continuously, within this angle range.

At the proximal end 11, the endoscope 10 has a first coupler 15 for optically coupling the endoscope 10 to a camera or an eyepiece, and a second coupler 16 for coupling the endoscope 10 to a light source via a light guide cable. From the second coupler 16, one or more light guides 30 lead through the shaft 14 to the distal end 11 of the endoscope 10. Illumination light generated by a light source can be transmitted via a light guide cable, the second coupler 16 and the light guide or guides 30 to the distal end 11 of the endoscope 10.

FIGS. 2 to 7 show schematic representations of a plurality of alternative embodiments of the distal end 11 of the endoscope 10 explained above with the aid of FIG. 1. FIGS. 2 to 7 respectively show a section along a plane parallel to the plane of the drawing of FIG. 1 in a highly simplified representation. The shaft, or the housing, of the endoscope 10 is merely indicated by an outline. Rods, articulations and other mechanical devices for holding, guiding and/or moving the optical devices represented are not represented for the sake of clarity.

As already mentioned, each of the embodiments explained below with the aid of FIGS. 2 to 7 comprises a light guide 30, which extends from the second coupler 16 at the proximal end 12 to the distal end 11 of the endoscope 10. The light guide 30 comprises, for example, a light waveguide or a bundle of light waveguides. The light guide 30 is provided and formed in order to transmit illumination light to the distal end 11 of the endoscope 10. At the distal end 11 of the endoscope 10, the light guide 30 has a light exit surface 31 for output of illumination light. At the distal end 11 of the endoscope 10, the illumination light is distributed into a predetermined solid angle range by means of the devices explained below with the aid of FIGS. 2 to 7.

Figure 2:
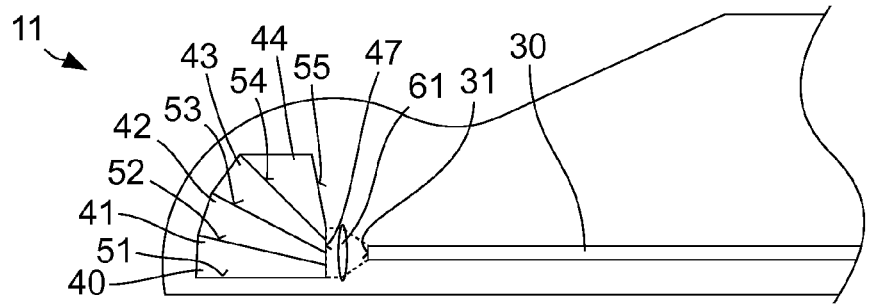
FIG. 2 shows a schematic representation of an embodiment of a distal end of an endoscope.

FIG. 2 shows a schematic representation of an embodiment of a light distribution device 40 at the distal end 11 of the endoscope 10. The light distribution device 40 comprises a plurality of prisms 41, 42, 43, 44 consisting of one or several different transparent materials. The prisms 41, 42, 43, 44 are joined to the light distribution device 40 for example by means of a cement, an adhesive or in another way. A reflective surface 52, 53, 54 is respectively arranged between each pair of neighboring prisms 41, 42, 43, 44. At the outermost prisms 41, 44, further reflective surfaces 51, 55 are arranged facing the reflective surfaces 52, 54. The light distribution device 40 comprises a light entry surface 47, which is coupled by means of a collimator to the light exit surface 31 of the light guide 30. The light entry surface 47 comprises a plurality of subregions, which are respectively formed by one of the prisms 41, 42, 43, 44.

The collimator 61 is formed and arranged in order to collimate the illumination light emerging from the light exit surface 31 of the light guide 30. To this end, the light exit surface 31 of the light guide 30 is arranged, in particular, at the focus of the collimator 61.

The reflective surfaces 51, 52, 53, 54, 55 are in particular planar, and have their smallest mutual spacing close to the light entry surface 47. Each individual reflective surface 51, 52, 53, 54, 55 may be partially transparent, i.e. it may have a reflectance and which lies for example in the range of from 0.2 to 0.4, in the range of from 0.4 to 0.6 or in the range of from 0.6 to 0.8. In particular, the outer reflective surfaces 51, 55 have a high reflectance of 0.9 or more, and the reflective surfaces 52, 53, 54 between the prisms 41, 42, 43, 44 respectively have an average reflectance in the range of from 0.3 to 0.7.

Alternatively, for example, all reflective surfaces 51, 52, 53, 54, 55 have a high reflectance of 0.9 or more. By using total reflection, it is possible to achieve a reflectance of 1. To this end, unlike in the representation in FIG. 2, gaps in which a gas, or another medium having a refractive index which is less than the refractive indices of the materials of the prisms 41, 42, 43, 44, is arranged are provided between the prisms 41, 42, 43, 44.

Illumination light emerging from the light exit surface 31 of the light guide 30 is collimated by the collimator 61 and enters the light distribution device at the light entry surface 47. By reflection at the reflective surfaces 51, 52, 53, 54, 55 arranged in the shape of a fan, the illumination light is fanned out in a direction parallel to the plane of the drawing of FIG. 2 in order to illuminate a spatial region, or a solid angle range, which occupies a substantially larger angle in a direction parallel to the plane of the drawing of FIG. 2 than in the direction perpendicular to the plane of the drawing of FIG. 2. The light distribution device 40 thus allows distribution of the illumination light in all possible fields of view of the endoscope 10 which correspond to the viewing directions 21 to 24.

Figure 3:
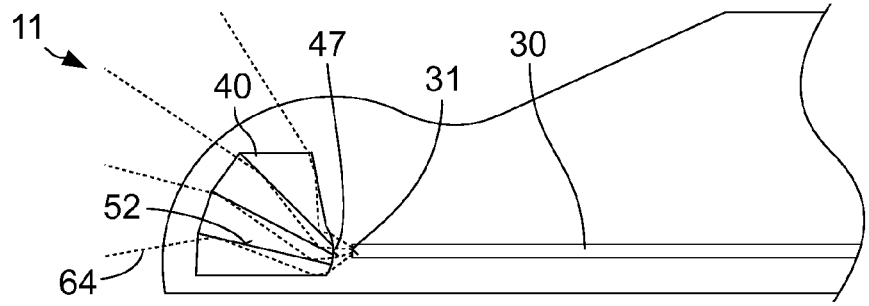
FIG. 3 shows a schematic representation of another embodiment of a distal end of an endoscope.

FIG. 3 shows a schematic representation of another embodiment, which in some features resembles the embodiment explained above with the aid of FIG. 2. In particular, a light distribution device 40 that comprises a plurality of prisms and a plurality of reflective surfaces is provided. With a view to clear representation, some features which resemble corresponding features of the embodiment of FIG. 2 are not provided with references in FIG. 3.

In contrast to the embodiment of FIG. 2, no collimator is provided. Instead, the light entry surface 47 is convexly curved and has a collimating effect, or at least the effect of reducing the divergence of the illumination light. In FIG. 3, a plurality of illumination light rays 64 are furthermore shown by dashed lines, in order to indicate the distribution of the illumination light by the light distribution device 40.

Figure 4:
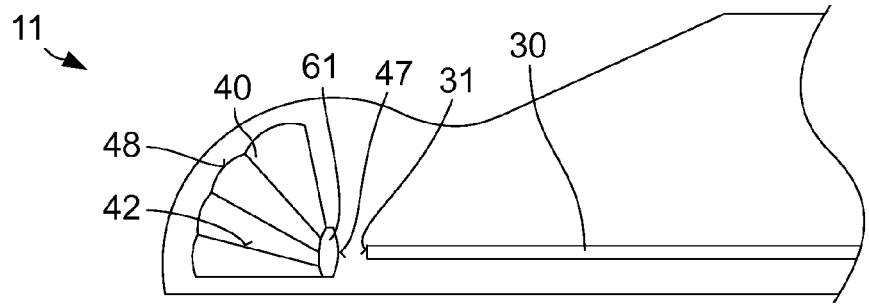
FIG. 4 shows a schematic representation of another embodiment of a distal end of an endoscope.

FIG. 4 shows a schematic representation of another embodiment, which resembles the embodiments of FIGS. 2 and 3 in some features. In particular, a light distribution device 40 that comprises a plurality of prisms and a plurality of reflective surfaces is provided. With a view to clear representation, some features which resemble corresponding features of the embodiment of FIG. 2 are not provided with references in FIG. 4.

The embodiment of FIG. 4 differs from the embodiments of FIGS. 2 and 3 inter alia in that a collimator 61, which is joined to the prisms of the light distribution device 40 or which is part of the light distribution device 40, is provided. The light entry surface 47 of the light distribution device 40 is therefore simultaneously the light entry surface of the collimator 61. The interface between the collimator 61 and the prisms of the light distribution device 40 may be locally planar as indicated in FIG. 4, or unlike in the representation of FIG. 4 it may be continuously curved or planar overall.

The light distribution device 40 represented in FIG. 4 furthermore differs from the embodiments of FIGS. 2 and 3 in that the light exit surface 48 of the light distribution device 40 is not locally planar, but locally curved convexly. In particular, the light exit surface 48 comprises a plurality of spherical, elliptical, toric or cylindrical sections respectively adjoining a single prism. The distribution of the illumination light emerging from the light distribution device 40 can be adjusted by the curvature of the light exit surface 48, or of the sections of the light exit surface 48 which adjoin the individual prisms. Unlike in the representation in FIG. 4, the light exit surface 48 may be locally concave.

Figure 5:
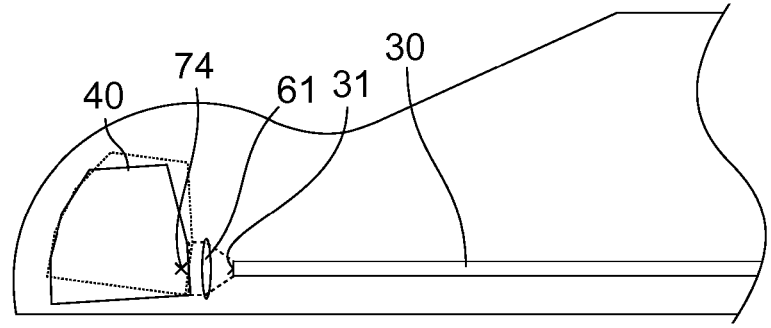
FIG. 5 shows a schematic representation of another embodiment of a distal end of an endoscope.

FIG. 5 shows a schematic representation of another embodiment, which in some features resembles the embodiments of FIGS. 2 to 4, in particular the embodiment of FIG. 2. In particular, a collimator 61 and a light distribution device 40 which correspond to the embodiment of FIG. 2 are provided. With a view to clear representation, some features which resemble corresponding features of the embodiment of FIG. 2 are not provided with references in FIG. 5. For the same reason, the reflective surfaces of the light distribution device 40 are not represented.

Unlike in the embodiment of FIG. 2, the light distribution device 40 can be pivoted about a pivot axis 74. The pivot axis 74 is perpendicular to the plane of the drawing of FIG. 5 and, in particular, parallel to the pivot axis, represented in FIG. 1, of the viewing direction of the endoscope. The contour of the light distribution device 40 is represented in two different positions in FIG. 5, on the one hand by a solid line and on the other hand by a broken line.

The distribution of the illumination light can be modified by pivoting the light distribution device 40 about the pivot axis 74. In the embodiment of FIG. 5, the pivot axis 74 is arranged close to the light entry surface of the light distribution device 40. In contrast thereto, the pivot axis may be arranged at a different position inside or outside the contour of the light distribution device 40.

Figure 6:
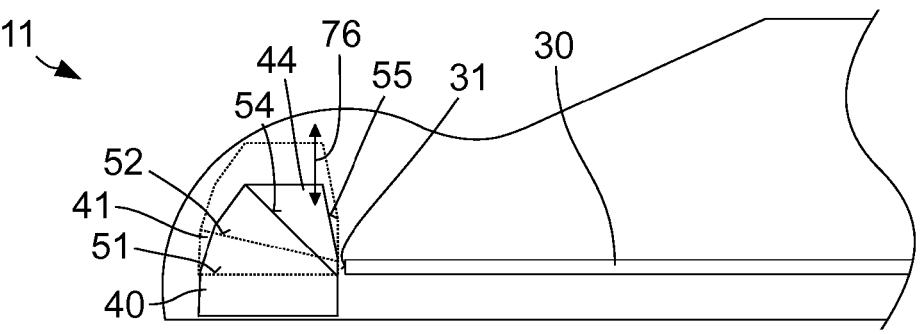
FIG. 6 shows a schematic representation of another embodiment of a distal end of an endoscope.

FIG. 6 shows a schematic representation of another embodiment, which in some features resembles the embodiment of FIG. 2. In particular, a light distribution device 40 which corresponds to the light distribution device explained above with the aid of FIG. 2 is provided. With a view to clear representation, some features which resemble corresponding features of the embodiment of FIG. 2 are not provided with references in FIG. 2. For the same reason, the reflective surfaces of the light distribution device 40 are only partially represented.

In contrast to the embodiment of FIG. 2, no collimator is provided. The embodiment of FIG. 6 furthermore differs from the embodiment of FIG. 2 in that the light distribution device can be displaced in a direction 76. The direction 76 is, in particular, perpendicular to the longitudinal axis, represented above with the aid of FIG. 1, of the endoscope and parallel to the plane of the drawing of FIG. 6. Alternatively, the light distribution device 40 may be displaceable along a curved path.

The light distribution device 40 is represented in two positions in FIG. 6, on the one hand by a solid line and on the other hand by a broken line. With a view to clear representation, besides the contour of the light distribution device 40, only two reflective surfaces 51, 52, and respectively 54, 55, are represented and provided with references in each case.

Owing to the short distance between the light exit surface 31 of the light guide 30 and the light entry surface of the light distribution device 40, and owing to the light exit surface 31 of the light guide 30 which is small in comparison with the light entry surface of the light distribution device 40, illumination light emerging from the light exit surface 31 of the light guide 30 is respectively coupled predominantly into only one prism of the light distribution device 40 in the two positions of the light distribution device 40 which are represented. In the position of the light distribution device 40 represented by a broken line, illumination light is predominantly coupled into the prism 41 between the reflective surfaces 51, 52, while in the position of the light distribution device 40 represented by a solid line, illumination light is predominantly coupled into the prism 44 between the reflective surfaces 54, 55.

By displacing the light distribution device 40 along a straight or—unlike in the representation of FIG. 6—curved path, the distribution of the illumination light can thus be influenced. The distribution of the illumination light may, in particular, be influenced in that the illumination light is coupled into different prisms, and consequently reflected at reflective surfaces which are orientated differently.

Figure 7:
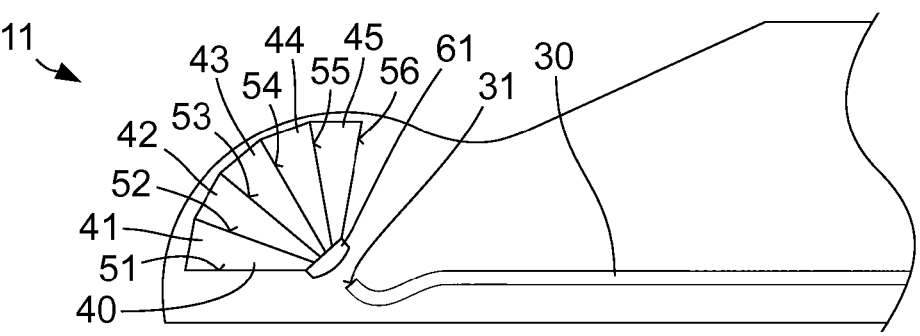
FIG. 7 shows a schematic representation of another embodiment of a distal end of an endoscope.

FIG. 7 shows a schematic representation of another embodiment, which in some features resembles the embodiments represented above with the aid of FIGS. 2 to 4. In particular, a light distribution device 40 that comprises a plurality of prisms 41, 42, 43, 44, 45 and a plurality of reflective surfaces 51, 52, 53, 54, 55, 56 is provided. Similarly as in the embodiment of FIG. 4, a collimator 61 which is joined to the prisms 41, 42, 43, 44, 45 of the light distribution device 40, or which is part of the light distribution device 40, is provided. Unlike in the embodiment of FIG. 4, the light distribution device 40, including the collimator 61, is essentially symmetrical with respect to a plane which is perpendicular to the plane of the drawing of FIG. 7 and intersects the longitudinal axis of the endoscope at an angle of from 40 degrees to 50 degrees in the example represented. The light guide 30 furthermore has a curvature at the distal end. The light exit surface 31 of the light guide 30 is arranged and orientated in such a way that illumination light emerging from the light exit surface 31 of the light guide 30 strikes the collimator 61.

Some features of the embodiments represented above with the aid of FIGS. 2 to 7 may be combined with one another in a different way, for example the convex or concave curvature of the light entry surface, the convex or concave curvature of the light exit surface of the light distribution device, the embodiment and arrangement of the collimator, the pivotability or displaceability and the curvature of the light guide close to its light exit surface. Furthermore, unlike in the representation of FIGS. 2 to 5 and 7, a collimator, or a convex light entry surface of the light distribution device with a collimating effect, may be obviated in order to bring about a different distribution of the illumination light. In particular, as an alternative a lens or a corresponding curvature of the light entry surface of the light distribution device may be provided, which does not or only insubstantially reduces, or even increases, the divergence of the illumination light emerging from the light exit surface of the light guide.

In all embodiments explained above with the aid of FIGS. 2 to 7, instead of a coupler for coupling the endoscope to an external light source, an internal light source may be provided at the proximal end of the endoscope. Furthermore, a light source may alternatively be provided at the distal end 11 of the endoscope, instead of the light guide 30.

Unlike in the embodiments explained above with the aid of FIGS. 2 to 7, the light distribution device may comprise non-prismatic transparent bodies instead of prisms. In this way, in particular, reflective surfaces curved in one or two directions may be produced between the transparent bodies.

Furthermore, unlike in the explanations above with the aid of FIGS. 2 to 7, the light distribution device may not comprise prisms. In this case, for example, in a similar way to conventional household mirrors, the reflective surfaces are arranged on thin glass panes, which may be mirrored on one or both sides.

REFERENCES 10 endoscope
11 distal end of the endoscope 10

12 proximal end of the endoscope 10
14 shaft of the endoscope 10
15 first coupler
16 second coupler
18 longitudinal axis of the endoscope 10
20 surface of a window component
21 first extreme viewing direction (0°)
22 second extreme viewing direction (120°)
28 pivot axis of the viewing direction
29 angle range of the viewing directions
30 light guide
31 light exit surface at the distal end of the light waveguide 30
40 light distribution device
41 first prism of the light distribution device 40
42 second prism of the light distribution device 40
43 third prism of the light distribution device 40
44 fourth prism of the light distribution device 40
45 fifth prism of the light distribution device 40
47 light entry surface of the light distribution device 40
48 light exit surface of the light distribution device 40
51 first reflective surface of the light distribution device 40
52 second reflective surface of the light distribution device 40
53 third reflective surface of the light distribution device 40
54 fourth reflective surface of the light distribution device 40
55 fifth reflective surface of the light distribution device 40
56 sixth reflective surface of the light distribution device 40
61 collimator
62 lens component
64 illumination light ray
70 illumination beam path
71 light propagation direction in the illumination beam path 70
72 light propagation direction in the illumination beam path 70
73 light propagation direction in the illumination beam path 70
74 pivot axis of the light distribution device 40
76 direction of the displaceability of the light distribution device 40

The invention claimed is:

1. An endoscope having a viewing direction configured to be pivoted relative to the endoscope, comprising:
an illumination beam path for transmitting illumination light;
a plurality of reflective surfaces for reflecting illumination light, the reflective surfaces being arranged at least partially next to one another in the illumination beam path relative to the intended light propagation direction of illumination light in the illumination beam path.

2. The endoscope of claim 1, wherein the reflective surfaces are arranged in the shape of a fan.

3. The endoscope of claim 1 wherein surface normals of planar reflective surfaces of the plurality of reflective surfaces lie in a plane perpendicular to a pivot axis of the viewing direction.

4. The endoscope of claim 1, wherein local surface normals of reflective surfaces in the central regions of the reflective surfaces lie in a plane perpendicular to a pivot axis of the viewing direction.

5. The endoscope of claim 1, wherein a reflective surface of the plurality of reflective surfaces has a reflectance of at most 0.75.

6. The endoscope of claim 1, wherein the reflective surfaces are at least either pivotable about an axis or displaceable along a path.

7. The endoscope of claim 6, wherein the illumination of the reflective surfaces is dependent on the position of the reflective surfaces adjusted by pivoting or displacing the reflective surfaces.

8. The endoscope of claim 1, wherein the plurality of reflective surfaces are rotatable relative to the endoscope.

9. An endoscope having a viewing direction configured to be pivoted relative to the endoscope, comprising:
an illumination beam path for transmitting illumination light; a plurality of reflective surfaces for reflecting illumination light, the reflective surfaces being arranged at least partially next to one another in the illumination beam path relative to the intended light propagation direction of illumination light in the illumination beam path; and
a light distribution device which comprises a plurality of transparent bodies, the reflective surfaces being present at interfaces respectively between two adjacent transparent bodies.

10. The endoscope of claim 8, wherein sections of a light entry surface of the light distribution device, which adjoin individual transparent bodies of the light distribution device, are planar.

11. The endoscope of claim 8, wherein sections of a light exit surface of the light distribution device, which adjoin individual transparent bodies of the light distribution device, are planar.

12. The endoscope of claim 9, wherein the transparent bodies are prisms made of a transparent material.

13. The endoscope of claim 12, wherein sections of a light exit surface of the light distribution device, which adjoin individual transparent bodies of the light distribution device, are planar.

14. The endoscope of claim 8, wherein sections of a light exit surface of the light distribution device, which adjoin individual transparent bodies of the light distribution device, are curved.

* * * * *